United States Patent [19]

Clad

[11] Patent Number: 4,608,147

[45] Date of Patent: Aug. 26, 1986

[54] APPARATUS FOR THE ELECTRO-ELUTION AND COLLECTING OF ELECTRICALLY CHARGED MACROMOLECULES IN A TRAP

[75] Inventor: Andreas Clad, Freiburg, Fed. Rep. of Germany

[73] Assignee: Carl Schleicher & Schuell GmbH & Co. KG, Einbeck, Fed. Rep. of Germany

[21] Appl. No.: 637,922

[22] Filed: Aug. 6, 1984

[30] Foreign Application Priority Data

Oct. 17, 1983 [DE] Fed. Rep. of Germany ....... 3337669

[51] Int. Cl.$^4$ ..................... B01D 13/02; G01N 27/28
[52] U.S. Cl. ................................ 204/301; 204/182.3; 204/182.6
[58] Field of Search ................ 204/180 R, 301, 182.3, 204/182.6

[56] References Cited

U.S. PATENT DOCUMENTS

| | | | |
|---|---|---|---|
| 3,079,318 | 2/1963 | Bier | 204/301 |
| 3,359,194 | 12/1967 | Kollsman | 204/301 |
| 3,392,100 | 7/1968 | Kollsman | 204/301 |
| 3,989,613 | 11/1976 | Gritzner | 204/301 |

OTHER PUBLICATIONS

Clad, A., et al., "A Cheap, Time- and DNA-Saving Device for the Electrophoretic Elution of DNA from Gels", *Analytical Biochemistry*, vol. 124, pp. 299–302, (1982).

*Primary Examiner*—John F. Niebling
*Assistant Examiner*—B. J. Boggs, Jr.
*Attorney, Agent, or Firm*—Jordan and Hamburg

[57] ABSTRACT

In an electro-elution apparatus for operation in an electrophoresis chamber and for the electro-elution of biological macromolecules from sections of electrophoresis gel, the macromolecules which are to be eluted are not temporarily adsorbed in a gel, but can be collected between two polymer membranes in a trap and pipetted out of the latter. The membrane, which is the first or inner membrane in the direction of migration of the macromolecules, is here permeable to the macromolecules under the action of the electric field, while the membrane, which is the second membrane in the direction of migration, namely the outer membrane of the electro-elution apparatus, is impermeable to the macromolecules under the same conditions. After the electric field has been switched off, both membranes are at least substantially impermeable to any mass transfer.

18 Claims, 5 Drawing Figures

APPARATUS FOR THE ELECTRO-ELUTION AND COLLECTING OF ELECTRICALLY CHARGED MACROMOLECULES IN A TRAP

DESCRIPTION

The invention relates to an apparatus for the electro-elution of electrically charged macromolecules.

Specifically, the invention relates to a process for the electro-elution of biological macromolecules, which as a rule are electrically charged, from electrophoresis gels.

An apparatus of this type has been disclosed in the journal Analytical Biochemistry 124, 299 to 302 (1982). The known apparatus is a plate-shaped cuboid of polyacrylate glass, in which several mutually parallel elution channels are formed in the shape of U-grooves which extend continuously from one side of the cuboid up to the opposite side and are open at the top. In one end region of each of the elution channels, nylon gauze in the form of a bag is inserted, which is hermetically sealed in the manner of a filter from the channel walls and is filled with an adsorption gel for the macromolecules, for example DNA, RNA, proteins or lipopolysaccharides.

The problem of electro-elution arises when the electrophoresis gels, in which macromolecules are usually fractionated, are worked up. The piece of electrophoresis gel containing the target fraction is cut out and placed into the channel of the electro-elution apparatus. The apparatus is then placed into a horizontal electrophoresis chamber in such a way that the electric field, which can be generated in the electrophoresis chamber, is parallel to the elution channel of the electro-elution apparatus. The electrophoresis chamber is then filled with a buffer to a level just below that at which there is a flow over the separating walls located between the mutually parallel channels. When the electric field is switched on, the electrically charged biological macromolecules migrate out of the electrophoresis gel lying in the buffer and are collected in the adsorption gel placed in the nylon bag. When the elution is complete, the elution gel is removed from the nylon bags and eluted on a column out of this adsorption gel and, in particular when the conventional malachite green gel is used, as a rule by means of a one-molar sodium perchlorate solution.

The complete procedure for this process, which at present is the best known to the state of the art, requires approximately forty minutes per piece of electrophoresis gel and, due to the repeated adsorption and elution, entails significant losses of target substance. Even if bacterial losses are disregarded, a total loss of target substance of at least about 25% must be expected in this elution process, that is to say at best a yield of approximately 75%, relative to the weight of the macromolecules in the initially introduced piece of electrophoresis gel, can thus be expected. In addition, the costs of the temporary adsorption gel are considerable. Thus, the commercial price for 25 ml of malachite green gel is, for example, about DM 350.00.

In the light of this state of the art, it is the object of the invention to provide an apparatus for the electro-elution of electrically charged macromolecules, in particular biological macromolecules, which permits rapid, loss-free and inexpensive elution of macromolecules, in particular from electrophoresis gels. In the sense of this object and in the sense of the present invention, the terms "elution" or "electro-elution" are to be understood also as the "elution" of the macromolecules from liquid phases under the action of an electric field, that is to say in particular the concentrating of solutions, desalination or transfer into a different buffer.

To achieve this object, the invention provides an apparatus for electro-elution, wherein the trap for the target macromolecules is bounded or formed by two polymer membranes. Of these two membranes, that which is the outer one relative to the longitudinal axis of the elution channel is permeable in the presence of an electric field to small ions and molecules, in particular to buffer and water, but is impermeable to the macromolecules which are to be eluted. That membrane which is the inner one in this sense, however, is permeable to all ions and molecules, that is to say in particular also to the macromolecules to be eluted, if this membrane is located in an electric field. With the electric field switched off, however, both membranes are impermeable to any ions and molecules of whatever size, that is to say, in particular, they are virtually water-tight. With the electro-elution medium made up and the electric field switched on, the macromolecules are thus extracted, for example, from the initially introduced piece of electrophoresis gel, migrate through the inner membrane in the direction of the electric field, as a rule towards the positive pole, and are retained and collected, that is to say concentrated, on the inside of the outer membrane, whereas the buffer ions migrate through this membrane into the electrophoresis chamber.

For operation, the apparatus according to the invention is placed into the electrophoresis chamber in the same way as the known apparatus described above. After the elution process has been completed, the polarity of the electric field is briefly reversed, preferably for ten to fifteen seconds, so that the macromolecules collected, and sometimes also partially adsorbed, on the inner surface of the outer membrane are detached from the membrane surface and released into the trap space.

With this apparatus, the electro-elution of a piece of electrophoresis gel takes not more than five minutes. The yield of eluted macromolecules is here at least 90% and can be virtually 100%. This yield can be obtained because the inner membrane used is a membrane which is water-tight and thus additionally bacterial-tight, that is to say it does not allow any bacteria to be transferred from the elution channel or the elution chamber into the trap. If the trap was carefully sterilized beforehand, a loss of macromolecules due to bacterial attack, which can take place to a considerable extent in all known electro-elution processes, can be eliminated in this way.

A great variety of membranes which meet the requirements stated above are commercially available in the most diverse shapes. Preferably, polymer membranes are used, the structure of which is based on polymers which can be wetted by water and the buffer solutions used, such as, in particular, cellulose, cellulose derivatives, polyamides, polyimides and polysulfones. Preferably, membranes of cellulose acetates are used as the outer membranes and those of regenerated cellulose are used as the inner membranes. Such membranes are available, for example, from the assignee of this application, under the type descriptions RAB or RAC for the outer membrane and RSB for the inner membrane. A large selection of the cellulose membranes to be used here can, however, also be obtained from any other manufacturer. The inner membrane should here have a mean pore size in the region of about ≲0.2 μm, in particular a pore size in the range from 0.05 to 0.20 μm, and the outer membrane should be impermeable to macromolecules having a molecular weight greater than approximately 1,000. It is, however, self-evident that such data are to be regarded only as guide values which can and will readily be changed by the user in accordance with the particular problem to be solved.

According to an embodiment of the invention, the macromolecule traps formed by the particular inner membrane and the particular outer membrane are provided on the two end regions of the continuously open elution channel, so that a separate elution chamber is formed between the two mutually opposite inner membranes in each case. This enables a buffer solution different from that in the electrophoresis chamber, in which the apparatus according to the invention is operated, to be used in the elution chamber. This makes it possible to desalinate the macromolecule solution or to change the buffer.

The membranes are preferably mounted exchangeably in the body of the apparatus. The exchangeability can here be obtained in particular by inserting or pushing the membrane from above into corresponding guides or recesses in the apparatus body. Above all for the membranes located on the inside, it has here proved to be convenient, handy and 100% reliable, if the inner membrane is surrounded by a frame of swellable material and this frame, in the dry and unswollen state, can be pushed with an exact fit into a U-shaped slotted guide open at the top. After the elution chamber has been filled with elution medium, or the apparatus has been placed into the horizontal electrophoresis chamber, the elution medium flows around the frame and causes it to swell, so that the inner membrane is clamped like a filter, making a seal, into the channel walls.

The outer membrane, which can also be used unframed, preferably bears from the outside against a separating wall which bounds the trap axially outwards. In this solid separating wall, a central bore which is covered by the membrane is provided for the passage of the ion-current. The membrane is here clamped or pressed against the separating wall and over the hole by a frame which in turn is stressed axially inwards, relative to the channel of the apparatus, for example by means of a compression spring or a tensioning screw or tensioning-screw sleeve. The seal between the outer membrane and this separating wall can additionally be improved by one or more sealing rings or sealing edges. Preferably, a continuous channel, which opens conically outwards, is here formed in the frame and in the tensioning-screw sleeve in order to avoid the formation of gas bubbles.

The body of the apparatus according to the invention is preferably made from an inert plastic, for example from a polycarbonate or an acrylic glass. Preferably, the plastic is suitable for autoclaving.

The invention is explained in more detail below by reference to an illustrative embodiment in conjunction with the drawings, in which.

Figure 1:
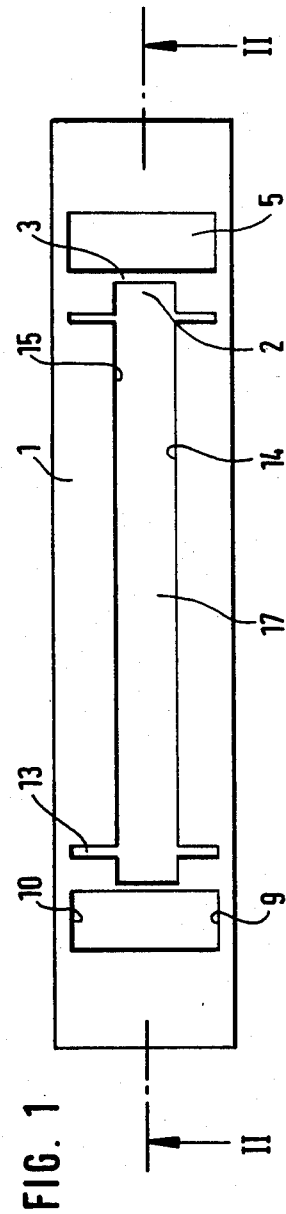
FIG. 1 shows, in plan view, an illustrative embodiment of the electro-elution apparatus without membranes.
Figure 2:
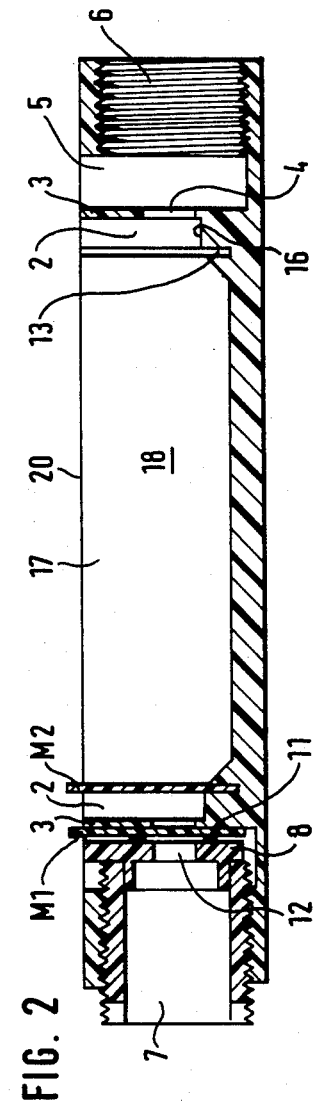
FIG. 2 shows a section along II—II in FIG. 1.

FIG. 1 shows the plan view of an illustrative embodiment of the electro-elution apparatus according to the invention or, more precisely, the body 1 of such an apparatus. FIG. 2 shows an axial section of this illustrative embodiment, the outer membrane M1 and the inner membrane M2 having been inserted on the left in the representation of FIG. 2. The body 1 consists of transparent polycarbonate. The membrane M1 is a cellulose acetate membrane which is impermeable to molecules having a molecular weight of greater than 1,000, even in the presence of an electric field. The inner membrane M2 is a simple cellulose membrane of a pore size of 0.2 μm. The space defined and bounded between the membranes M1 and M2 serves as the trap 2 for the macromolecules which are to be eluted. Axially outwards, the trap 2 is bounded by a separating wall 3 which is formed integrally from the body 1. In the separating wall 3, a relatively large orifice 4 is provided which ensures a free connection between the trap 2 and the surroundings. Specifically, the orifice 4 opens into a recess or prechamber 5 which is cut out with an open top and is axially open towards the end face of the body 1 via a bore which has an internal thread 6. With the apparatus in operation, this prechamber 5 is preferably filled with air. For this purpose, the a tensioning sleeve 7 with an external thread must be formed in such a way that, after screwing into the internal thread 6, the system is waterproof outwards, that is to say into the prechamber 5. A tensioning frame 8 which is guided, secure against rotation, on the side walls 9, 10 of the prechamber 5 is, axially inwards, inserted into and pushed over the tensioning sleeve 7. Around its circumference, the tensioning frame 8 has a sealing and cutting edge, the clear diameter of which is somewhat greater than the diameter of the orifice 4. When the tensioning sleeve 7, with the tensioning frame 8 inserted, is screwed into the body 1, the tensioning frame 8 is guided towards the separating wall 3. At the same time, the membrane M1 inserted from above and the orifice 4 are clamped in between the tensioning frame 8 and the separating wall 3, making a tight seal. By means of the sealing and cutting edge 21, the membrane M1 itself is here used as a gasket.

An orifice 12, aligned with the orifice 4, in the tensioning frame 8 ensures free flow of current through the membrane M1. The orifice 12 in the tensioning frame and the neighbouring orifice 21 in the tensioning sleeve form a cylindrical channel (FIG. 2) or, preferably, widen conically outwards (FIG. 5) and thus prevent the persistence of gas bubbles in front of the membrane M1. The tensioning sleeve 7 with an external thread can be screwed into the internal thread 6, and the tensioning frame 8 which is guided, secure against rotation, on the side walls 9, 10 (FIG. 1) of the prechamber 5 is axially inwards inserted telescopically into and pushed over the tensioning sleeve. By screwing the tensioning sleeve 7 in, the tensioning frame 8 is guided towards the separating wall 3 or forced onto it. At the same time, the outer membrane M1 insertable from above into the prechamber 5 is clamped in, firmly and tightly sealing the orifice 4, between the tensioning frame 8 and the separating wall 3. The tightness of this clamping can be improved by additional sealing rings 11. The orifice 12, aligned with the orifice 4, in the tensioning frame 8 ensures a free flow of current through the membrane M1. Since the prechamber 5 is kept free of liquid, the tightness of the trap 2 towards the prechamber 5 can be monitored in an optimum manner, and the formation of tracking current paths can be excluded.

Axially inwards, the boundary of the trap 2 is fixed by a U-shaped slotted groove 13 which is open at the top and into which the inner membrane can be inserted from above. The U-shaped slotted groove 13 is here formed both in the side walls 14, 15 and in the floor 16 of the channel 17.

The membrane M2 is provided with a frame-like edge zone which, in the dry state, can be inserted with an exact fit into the slotted groove 13. When the elution medium is introduced into the channel 17, the frame of the membrane M2 swells, so that the membrane is retained in the slotted groove 13 with a hermetically sealed press fit.

Between the two inner membranes M2, a section, serving as the elution chamber 18, of the continuous channel 17 is separated off by these membranes. On the one hand, the elution chamber 18 is electrically connected to the outer electrolyte of the electrophoresis chamber via the membranes M1 and M2 and the orifices 4 and 12 but, on the other hand, it is hydrodynamically and chemically separated from the surroundings to such an extent that it is quite possible to fill the elution chamber 18 with an electrolyte or buffer of a composition which is substantially different from that of the electrolyte used in the electrophoresis chamber.

For operation, the gel piece which is to be eluted and which contains the macromolecules, is placed into the elution chamber 18 of the electro-elution apparatus. The two traps 2 and the elution chamber 18 are then filled with a highly dilute buffer or with distilled water, namely in such a way that the level 19 (FIG. 3) of the medium filled in is just below the upper edge 20 (FIG. 2) of the chamber 18 or the body 1. The apparatus is then placed into a horizontal electrophoresis chamber which is filled with so much buffer solution that the level of the buffer solution in the electrophoresis chamber is at least essentially the same as the level 19 in the elution chamber. However, the concentration of the buffer solution in the electrophoresis chamber can here be substantially greater, as a rule ten to a hundred times greater, than the concentration of the buffer in the elution medium.

Figure 3:
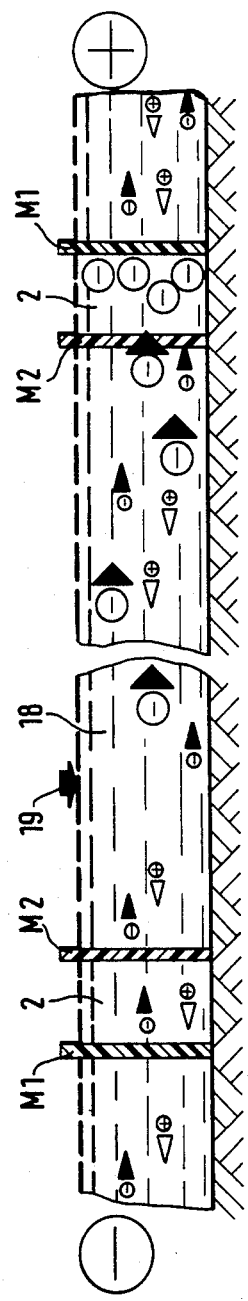
FIG. 3 shows a diagrammatic representation of the mode of action of the apparatus illustrated in FIGS. 1 and 2.

Moreover, the electro-elution apparatus is placed into the electrophoresis chamber in such a way that the electric field, which can be generated in the electrophoresis chamber, is at least substantially parallel to the channel 10. This is shown diagrammatically in FIG. 3. In the illustration in FIG. 3, the minus signs surrounded by a large circle here denote negatively charged macromolecules, whilst the plus signs and minus signs surrounded by a small circle denote the buffer ions. In the presence of the electric field, the polarity of which is assumed to be as shown in FIG. 3, the ions migrate in the directions shown in FIG. 3 by short arrowheads, namely the positive buffer ions migrate to the negative pole, and the negative buffer ions and the negatively charged macromolecules migrate to the positive pole of the acting electric field. At the same time, all the negatively charged particles pass through the membrane M2 into the trap 2. However, whilst the negatively charged buffer ions then also pass through the outer membrane M1 under the action of the field and are thus transferred into the buffer of the electrophoresis chamber, the electrically charged macromolecules are retained on the axially inward surface of the outer membrane M1.

In this way, all the electrically charged macromolecules are gradually collected on the membrane M1. After the elution has been completed and all the electrically charged macromolecules have been transferred from the elution chamber 18 into the trap 2, the polarity of the field is reversed for about ten to fifteen seconds, so that the macromolecules collected on the outer membrane M1 are released and migrate into the trap 2, from where they can readily be removed in high concentration from above, for example by means of a micropipette.

The volume ratio of each individual trap 2 and the elution chamber 18 is approximately 1:100. However, since the trap 2 must not be made so narrow that it is no longer accessible, for example, to a pipette, the volume reduction is effected in the manner shown in FIG. 2 by raising the floor or bottom of the trap 2 relative to the floor of the elution chamber 18.

Figure 4:
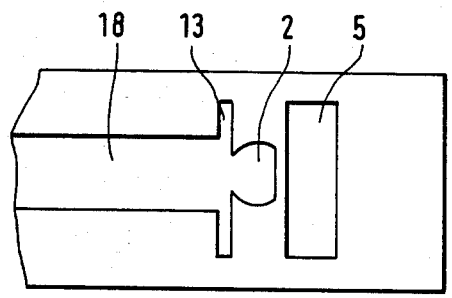
FIG. 4 shows a further illustrative embodiment of the electro-elution apparatus, in a partial representation and in plan.
Figure 5:
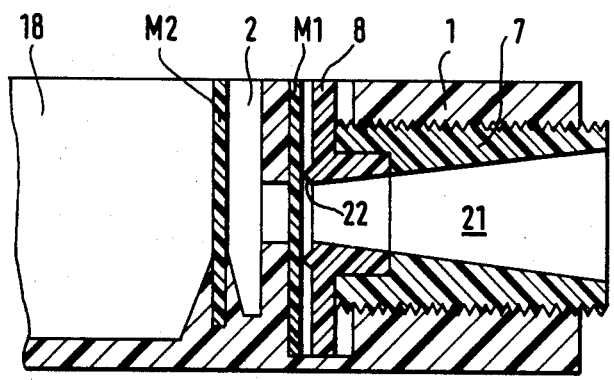
FIG. 5 shows an axial section of the apparatus shown in FIG. 4.

Alternatively, the volume of the trap can be reduced by the methods evident from FIGS. 4 and 5, namely by making the trap 2 with a circular cross-section and a downward conical taper.

The further illustrative embodiment of the electro-elution apparatus, as shown in FIGS. 4 and 5, differs additionally from the apparatus shown in FIGS. 1 and 2 in that the channel 21, defined by the orifice 12 in the tensioning frame 8 and the interior of the tensioning sleeve 7, is made continuous and with outward-opening smooth walls. This prevents the formation or adhesion of gas bubbles in the channel 21 and hence changes in the electric current conditions.

Moreover, in the tensioning frame 8 shown in FIG. 5, a cutting ring edge 22 is formed, which forces the membrane M3 against the outside of the separating wall 3, making a seal.

I claim:

1. Apparatus for the electro-elution of electrically charged macromolecules, comprising a cuboid or plate-like body, said body having at least one elongate channel extending from one end to the opposite end of said body, said channel opening up at both ends of said body, said channel being open at least partially at the top of said body, an inner membrane disposed in at least one end portion of said body and extending generally transversely of the longitudinal axis of said channel, an outer membrane disposed in a position spaced from said inner membrane to define therebetween a section of said channel which forms a trap space, said outer membrane being permeable in the presence of an electric field to water and to small ions and molecules, and impervious to the macromolecules which are to be eluted, said inner membrane in the presence of an electric field being permeable to ions and molecules and therefore to the macromolecules to be eluted, the inner and outer membranes in the absence of an electric field being impermeable to water and buffers used with the apparatus, whereby macromolecules pass through said inner membrane into said trap space and are trapped in said trap space.

2. Apparatus according to claim 1 further comprising a second inner membrane disposed in the other end portion of said body, a second outer membrane disposed in a position spaced from said second inner membrane to form a second trap space for the macromolecules, the portion of said channel between the first said inner membrane and said second inner membrane defining an elution chamber.

3. Apparatus according to claim 1, wherein said inner and outer membranes are wettable by water and the buffer solutions used with the apparatus.

4. Apparatus according to claim 1, wherein said inner and outer membranes are polymer membranes.

5. Apparatus according to claim 1, wherein the materials for said inner and outer membranes are selected from the group consisting of cellulose, cellulose derivatives, polyamides, polyimides and polysulfones.

6. Apparatus according to claim 1, wherein said outer membrane comprises cellulose acetate and said inner membrane comprises regenerated cellulose.

7. Apparatus according to claim 1, wherein said body has a chamber opening up to the top of said body, at least one of the membranes being exchangeably inserted from the top of said body into said chamber.

8. Apparatus according to claim 1, wherein said body has guide slots opening to the top of said body, at least one of the membranes being exchangeably inserted from the top of said body into said guide slots.

9. Apparatus according to claim 8, wherein at least one of the membranes is mounted in a frame which is constructed to swell in the elution medium and which, in the dry unswollen state, fits into said guide slots so that the membrane mounted in said frame can be pushed with an exact fit into said guide slots.

10. Apparatus according to claim 1, wherein said body comprises an integrally formed impermeable separating wall having an orifice, said outer membrane being disposed against said separating wall and covering said orifice, and a frame means mounted in said body sealingly pressing said outer membrane against said separating wall.

11. Apparatus according to claim 10, wherein said frame means comprises a frame member and a tensioning sleeve, said frame member being disposed against said outer membrane, thread means on said body for receiving said tensioning sleeve, and a passage extending through said frame member and said tensioning sleeve.

12. Apparatus according to claim 11, wherein said passage has a partial conical configuration which continuously increases in diameter toward the end of said body.

13. Apparatus according to claim 1, wherein said trap space is open at the top of said body.

14. Apparatus according to claim 1, wherein said body defines an elution chamber on the side of said inner membrane opposite the side of said inner membrane which defines part of said trap, said trap having a volume approximately one hundred times less than the volume of said elution chamber.

15. Apparatus according to claim 1, wherein said apparatus is used for electro-elution from electrophoresis gels.

16. Apparatus according to claim 1, wherein said apparatus is used for concentrating and desalinating biological macromolecules.

17. Apparatus according to claim 1, wherein said apparatus is used for transferring macromolecules from one buffer to a different buffer.

18. Apparatus according to claim 1, wherein said apparatus is used for concentrating and separating positively charged proteins.

* * * * *